Figure 1:
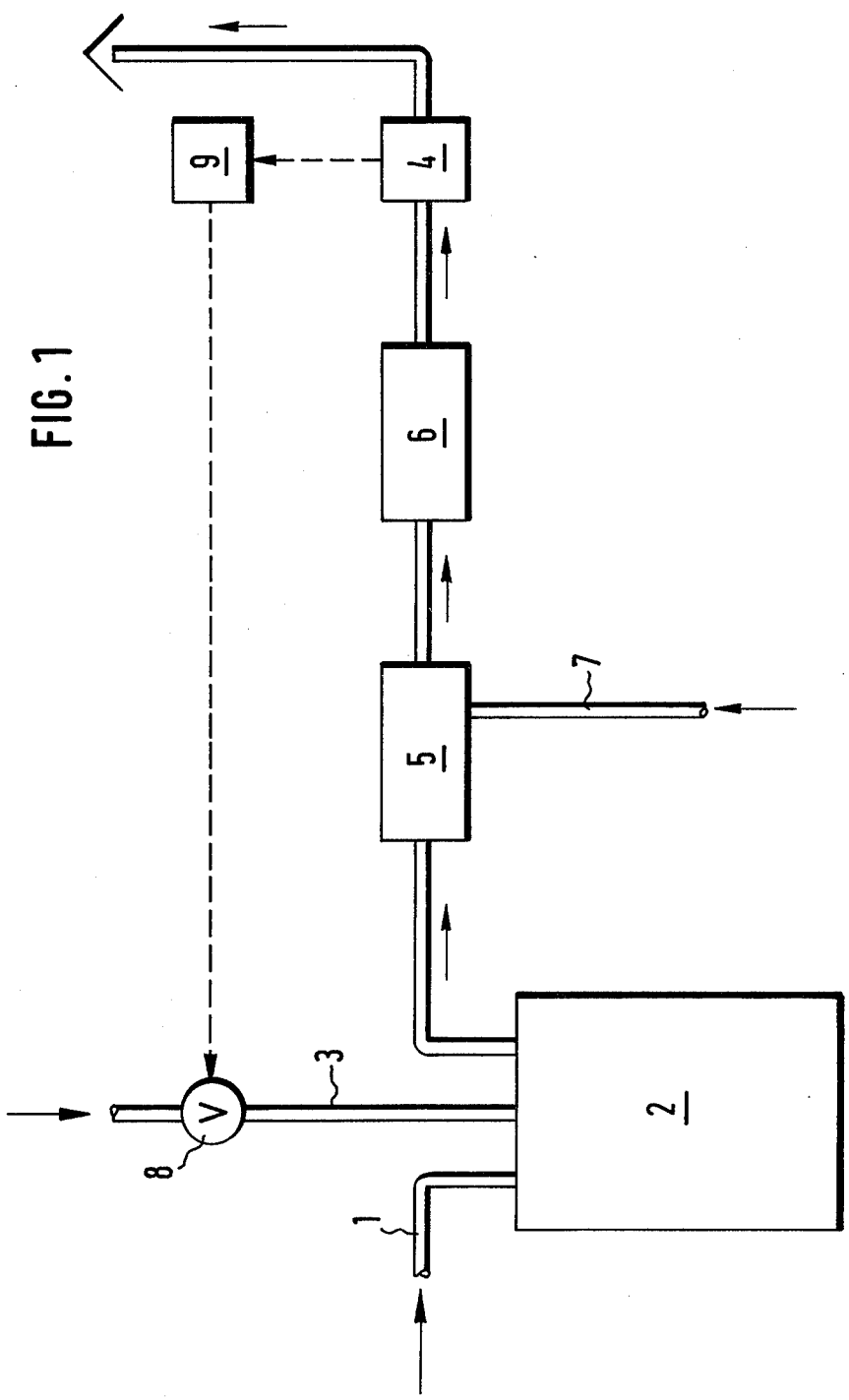

United States Patent [19]

Melzer et al.

[11] 4,244,695
[45] Jan. 13, 1981

[54] PROCESS FOR THE QUANTITATIVE DETERMINATION OF THE OXYGEN DEMAND OF WATER CONTAINING OXIDIZABLE MATTER

[75] Inventors: Werner Melzer, Liederbach; Dieter Jaenicke, Hofheim am Taunus, both of Fed. Rep. of Germany

[73] Assignee: Hoechst Aktiengesellschaft, Frankfurt, Fed. Rep. of Germany

[21] Appl. No.: 58,849

[22] Filed: Jul. 19, 1979

[30] Foreign Application Priority Data

Jul. 21, 1978 [DE] Fed. Rep. of Germany ....... 2832043

[51] Int. Cl.³ .................. G01N 31/12; G01N 33/18
[52] U.S. Cl. ................. 23/230 PC; 23/230 M; 23/906; 422/79
[58] Field of Search ............. 23/230 M, 230 PC; 422/79

[56] References Cited

U.S. PATENT DOCUMENTS

| 3,560,156 | 2/1971 | Teal et al. | 422/79 X |
| 3,607,071 | 9/1971 | Staffin et al. | 23/230 PC |
| 3,679,364 | 7/1972 | Teal et al. | 422/79 X |
| 3,933,429 | 1/1976 | Shibata et al. | 422/79 X |
| 3,958,937 | 5/1976 | Shibata et al. | 422/79 X |
| 4,074,973 | 2/1978 | Igaki et al. | 422/79 X |

FOREIGN PATENT DOCUMENTS 2313379  9/1973  Fed. Rep. of Germany ...... 23/230 PC

OTHER PUBLICATIONS

Butzelaar; P. F. et al., "A Method of Measuring the Oxygen Demand of Water"; Philips Tech. Rev. 34, 1974; No. 5/6, pp. 123–128.

Primary Examiner—Barry S. Richman
Attorney, Agent, or Firm—Curtis, Morris & Safford

[57] ABSTRACT

For the quantitative determination of the total oxygen demand of water containing oxidizable matter, the water is continuously evaporated at about 900° C. in the presence of varying amounts $l_1, \ldots, l_n$ of oxygen-containing gas added per unit of steam at continuously repeated intervals. The oxygen-containing gas should not exceed 1 to 5% by volume, calculated on the amount of steam produced during each interval. The residual oxygen concentrations $S_1, \ldots, S_n$ in the steam gas/mixture are measured for the different amounts of oxygen-containing gas added and the oxygen demand is calculated from the residual concentrations and the added amounts of the oxygen-containing gas.

2 Claims, 2 Drawing Figures

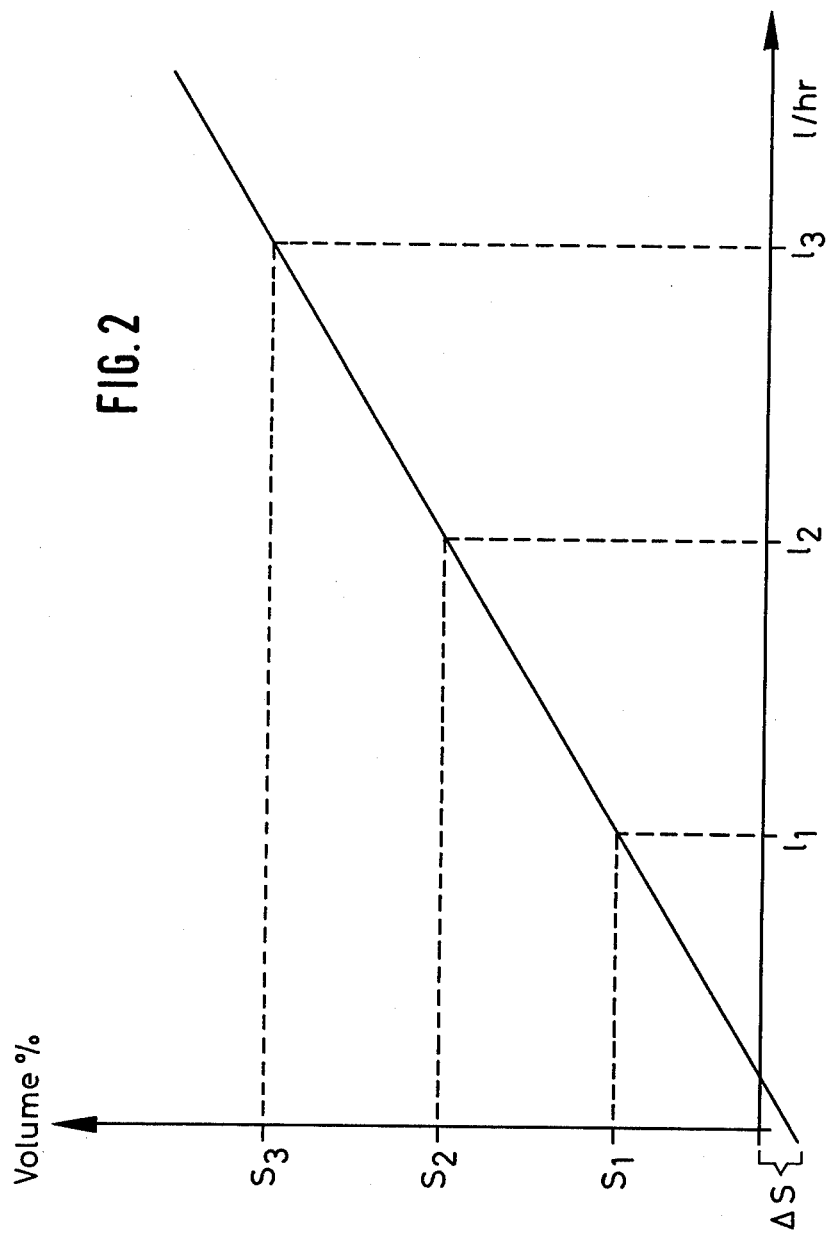

PROCESS FOR THE QUANTITATIVE DETERMINATION OF THE OXYGEN DEMAND OF WATER CONTAINING OXIDIZABLE MATTER

This invention relates to a process for the quantitative determination of the oxygen demand of water containing oxidizable matter by continuous evaporation of the water in the presence of oxygen at a temperature of about 900° C.

In the specification the following expressions are intended to mean:
the TOD value is the Total Oxygen Demand of the water containing oxidizable matter;
the oxygen-containing gas includes pure oxygen and all oxygen-containing gases, especially air.

According to a known process for the determination of the TOD value, water containing oxidizable matter is introduced in small portions into a large constant flow of oxygen-containing carrier gas heated to about 900° C. and evaporated. The proportion by volume of steam to carrier gas is about 1:100. In this process, oxidizable matter possibly contained in the water is oxidized. The decrease of the oxygen concentration is then measured in comparison with the starting carrier gas and the measured value is used to determine the TOD value. This method has the drawback that the water portions have to be dosed very exactly, especially in the case of strongly polluted waste water.

It is the object of the present invention to provide a process for the quantitative determination of the TOD value of water containing oxidizable matter in which the demands on the dosing accuracy of the water portions are very low.

This objective is achieved by a process which comprises (a) evaporating the water and adding to the steam at continuously repeated intervals varying amounts $l_1, \ldots, l_n$ of oxygen-containing gas per unit of steam, the respective amount of the oxygen-containing gas not exceeding 1 to 5% by volume, calculated on the amount of steam produced during the corresponding interval:

(b) measuring the residual oxygen concentrations $S_1$-$S_n$ for each amount of oxygen-containing gas $l_1, \ldots, l_n$ and (c) calculating the TOD from the residual concentrations $S_1, \ldots, S_n$ and the amounts of oxygen-containing gas $l_1, \ldots, l_n$ introduced in step (a).

To determine the TOD value from the measured residual oxygen concentrations $S_1, \ldots, S_n$ and the added amounts of oxygen-containing gas $l_1, \ldots, l_n$, the amounts of oxygen-containing gas are plotted in a diagram on the abscissa and the respective residual oxygen concentrations on the ordinate and the individual points obtained are linked to form a curve. The intersection of the curve with the ordinate indicates the decrease of the oxygen concentration with respect to the initial concentration. This decrease is directly proportional to the TOD value.

The TOD value can be calculated also by the equation $$TOD = \alpha \frac{1}{n} \Sigma \frac{S_1 l_n - S_n \cdot l_1}{l_n - l_1} ; n = 2, 3, \ldots$$

If care is taken that the temperature does not drop below the dew point, the steam containing oxygen-containing gas may be introduced directly into the oxygen analyzer. Alternatively, the steam containing oxygen-containing gas can be added in dosed quantities to a constant flow of oxygen-free carrier gas. Before the flow of carrier gas is introduced into the oxygen analyzer, the steam must be removed therefrom, for example by condensation. In this method, the volume ratio between steam and carrier gas should be kept as constant as possible.

The process according to the invention makes it possible to control in a particularly advantageous manner the content of oxidizable matter in waste water. It is also worth mentioning that the process is nearly insensitive to variations in the dosage rate of the water samples. With a volume ratio between steam and air of 100:1 and a variation of the water dosage by a factor 2, the error is only 1%, related to the measured TOD value.

The invention will now be described in further detail and by way of example only with reference to the accompanying drawing, FIG. 1 of which is a flow scheme of the process of the invention and;

FIG. 2 is a diagrammatical representation.

Water is continuously introduced into reaction vessel 2 through conduit 1 and varying amounts of air are supplied by means of a dosing device 8 through conduit 3. In the reaction vessel the water is evaporated at about 900° C. and the oxidizable matter is reacted with oxygen. The carrier gas should contain oxygen in such an amount that all oxidizable matter in the water is oxidized. About 1% by volume of oxygen, calculated on the volume of steam, proved to be sufficient. The steam containing the oxygen-containing gases leaving reaction vessel 2 is conveyed to an oxygen analyzer 4 (for example a zirconium oxide measuring cell) and the residual oxygen concentration in the mixture is determined.

In one embodiment of the process of the invention the steam containing the oxygen-containing gas is added through a dosing device 5 to a constant flow of carrier gas 7, for example in a ratio of 1:1. In a device 6 the steam is removed from the mixture of carrier gas and steam containing the oxygen-containing gas, for example by drying or condensation, and the oxygen content of the gas is then determined. In this embodiment condensation of the steam on its way from reaction vessel 2 to device 6 must be avoided.

The functions of device 9 are the regulation of air dosing device 8, the accurate synchronization of the different air doses with the respective residual oxygen concentrations and the determination of the TOD value.

Referring to FIG. 2, the amounts of oxygen-containing gas $l_1, \ldots, l_n$ in liter per hour are plotted on the abscissa and the pertaining residual oxygen concentrations $S_1, \ldots, S_n$ in % by volume are plotted on the ordinate. $\Delta S$ corresponds to the decrease of the oxygen concentration in the starting gas caused by the contaminants in the water and is directly proportional to the TOD value.

The following example illustrates the invention.

EXAMPLE

Water which was polluted by 1.28 g/l of methanol (corresponding to a TOD value of 1.92 g of $O_2$/l) was conveyed continuously by a pump at a rate of 100 g per hour into a reactor having a capacity of 200 cc and heated to 900° C. Oxygen was introduced into the reactor, first at a rate of $l_1 = 0.5$ l/hr and then at a rate of $l_2 = 1$ l/hr and in an oxygen analyzer heated to above $+100°$ C. the respective residual oxygen concentrations were determined. $S_1$ was found to be 0.30% by volume and $S_2$ 0.70% by volume.

Consequently, the decrease of the oxygen concentration resulting from the water contaminant was $$\Delta S = \frac{S_1 l_2 - S_2 l_1}{l_2 - l_1} = \frac{0.3 \cdot 1 - 0.7 \cdot 0.5}{1 - 0.5} = -0.1\ \%$$

by volume which corresponds to a TOD value of 1.92 g of $O_2$/l.

What is claimed is:

1. Process for the quantitative determination of the oxygen demand (TOD) of water containing oxidizable matter by continuously evaporating the water at about 900° C. in the presence of oxygen, which comprises
   (a) adding to the steam at continuously repeated intervals varying amounts $l_1, \ldots, l_n$ of oxygen-containing gas per unit of steam, the respective amount of the oxygen-containing gas not exceeding 1 to 5% by volume, calculated on the amount of steam produced during the corresponding interval;
   (b) measuring the residual oxygen concentration $S_1$–$S_n$ for each amount of oxygen-containing gas $l_1, \ldots, l_n$ and
   (c) calculating the TOD from the residual concentrations $S_1, \ldots, S_n$ and the amounts of oxygen-containing gas $l_1, \ldots, l_n$ introduced in step (a).

2. The process as claimed in claim 1, wherein the mixture of oxygen-containing gas and steam of step (a) is introduced into a constant flow of oxygen-free carrier gas, the steam is removed, whereupon steps (b) and (c) are carried out.